United States Patent [19] [11] 4,380,511
Mannuzza et al. [45] Apr. 19, 1983

[54] PURIFICATION OF BOVINE THROMBIN

[75] Inventors: Frank J. Mannuzza, Peotone; Joseph G. Montalto, Bradley, both of Ill.

[73] Assignee: Miles Laboratories, Inc., Elkhart, Ind.

[21] Appl. No.: 292,236

[22] Filed: Aug. 12, 1981

[51] Int. Cl.³ ................................................ C07G 7/00
[52] U.S. Cl. ................................. 260/112 B; 424/101
[58] Field of Search .................................... 260/112 B

[56] References Cited

U.S. PATENT DOCUMENTS 4,016,149 4/1977 Travis et al. .......................... 260/122
4,093,612 6/1978 Travis et al. ...................... 260/121 X

OTHER PUBLICATIONS

Remington's Pharmaceutical Sciences, 14th edition, pp. 1524–1525, (1970), K. E. Avis.
J. Pharm. Pharmac., 30:198–199, (1978), J. C. Cradock, et al., "Reduction of Pyrogens-Application of Molecular Filtration".
J. Biol. Chem., 243:112–117, (1968), E. T. Yin & S. Wessler, "Bovine Thrombin and Activated Factor X: Separation & Purification".
FEBS Letters, 51(1):191–194, (1975), R. Wallin & H. Pyrdz, "Purification of Bovine Prothombin by Affinity Chromatography".
Biochemica. et Biophysica. Acta., 222:691–695, (1970), "Separation of Blood Coagulation Factors II, VII, IX and X by Cel Filtration in the Presence of Dextran Blue", A. C. W. Swart and H. C. Hemker.
Biochemica. et Biophysica. Acta., 434:199–208, (1976), "Purification of Human Blood Clotting Factor X by Blue Dextran Agarose Affinity Chromatography", L. Vician & G. H. Tishkoff.
J. Chromatography, 69:209–214, (1972), "Affinity Chromatography of Phosphofructokinase Using Cibacron Blue".
J. Biol. Chem., 248:7729–7741, (1973), S. P. Bajaj and K. G. Mann, "Simultaneous Purification of Bovine Prothombin and Factor X: Activation of Prothrombin by Trypsin-Activated Factor X".
J. Biol. Chem., 250:8897–8906, (1975), M. R. Downing, R. J. Butkowski, M. M. Clark & K. G. Mann, "Human Prothrombin Activation".
Arch. Biochem., 5:265, (1944), E. C. Loomis and W. H. Seegers, "Purified Prothrombin: Factors Which Influence its Activation".
J. Biol. Chem., 246:6106–6114, (1971), K. G. Mann, C. M. Heldebrant and D. N. Fass, "Multiple Active Forms of Thrombin: II, Mechanism of Production from Prothrombin".
Biochemica, et. Biophysica. Acta., 261:284–289, (1972), E. Thye Yin, et al., "Picogram-Sensitive Assay for Endotoxin: Gelation of *Limulus polyphemus* Blood Cell Lysate Induced by Purified Lipopolysaccharides & Lipid A from Gram-Negative Bacteria", BBA Report 21325.

*Primary Examiner*—Howard E. Schain
*Attorney, Agent, or Firm*—James D. McNeil

[57] ABSTRACT

A method for removing pyrogenic material from bovine thrombin is disclosed. The method involves forming a complex of a blue dye and a polysaccharide and equilibrating the complex with a low ionic strength salt solution. Bovine thrombin is added to the complex. The pyrogenic material is removed from the bovine thrombin by washing the bovine thrombin with a low ionic strength salt solution, and the pyrogen-free bovine thrombin is recovered.

6 Claims, No Drawings

PURIFICATION OF BOVINE THROMBIN

BACKGROUND OF THE INVENTION AND PRIOR ART

This invention involves a process for removal of pyrogenic material from bovine thrombin.

Pyrogens can cause undesirable reactions in humans, including fever, chills, pains in back and legs and malaise. Because of these undesirable physiological reactions caused by the presence of pyrogens in animals, pharmaceutical preparations must be relatively free of pyrogens.

All biological products for parenteral prevention, diagnosis, or treatment of disease in man must meet specified tests, including a test for the presence of pyrogens. The pyrogen test as described by United States Pharmacopeia, is a biological test in which a fever response in rabbits is used as the criterion. Because the use of thrombin containing pyrogens in a topical application to produce localized clotting can introduce pyrogens into the body fluid systems, or the blood circulating system, such thrombin preparations must meet the same standards involving pyrogens as parenteral pharmaceutical preparations.

*Remington's Pharmaceutical Sciences,* Fourteenth Edition, pp. 1524–1525 (1970) emphasizes the difficulty of removing pyrogens from pharmaceutical preparations. The article indicates that the preferred procedure is to prevent the introduction of pyrogens into parenteral preparations, rather than attempt to remove them, a task which it indicates . . . "may well be virtually impossible."

*J. Pharm. Pharmac.,* 30: 198 (1978) indicates that methods previously suggested for removing pyrogens from a pharmaceutical dosage form include recrystallization; careful treatment in the presence in dilute alkali, acid or oxidizing agents; adsorption on charcoal, asbestos or other materials; anion exchange chromatography or silicic acid thin layer chromatography. The authors suggest that the above-named methods had value for laboratory usage in a small-scale, but did not provide optimal removal of pyrogens from an unstable drug on a multi-liter scale. The authors removed the pyrogen-contaminants by molecular filtration, which is an expensive procedure.

The prior art is replete with methods of purification of blood factors, including Factor II (prothrombin), Factor IIa (thrombin), and Factor X. The two major methods are ion exchange chromatography and affinity chromatography.

For example, *J. Biol. Chem.,* 243: 112–117 (1968) describes purification of thrombin by a stepwise chromatographic technique on diethylaminoethyl (DEAE) cellulose, to remove plasminogen and plasmin. *FEBS Letters,* 51(1): 191–194 (1975) describes purification of bovine trypsin and thrombin by affinity chromatography.

The most relevant prior art relating to purification of blood factors appears to be *Biochemica. et Biophysica. Acta.,* 222: 691–695 (1970) and 434: 199–208 (1976).

The 1970 article describes a method of purifying human blood clotting Factor X. Because prothrombin (Factor II) can be converted to thrombin (Factor IIa) by Factor Xa catalysis, the authors were concerned with obtaining Factor X free of other blood clotting factors, including thrombin. The method involved complexing a blue dye-polysaccharide complex and clotting factors and chromatographing. The method is based on the ionic strength-dependent association of clotting factors with the blue dye portion of the complex and subsequent gel filtrations. At low ionic strength, Factors II and IX were eluted in the void volume, indicating that they were complexed with the blue dye-polysaccharide. Factors VII and X were eluted in the included volume, indicating that they were not complexed with the blue dye-polysaccharide complex. The structure of the blue dye used was identified in *J. Chromatography,* 69: 201–214 (1972) as having a 4-phenylamino-1-amino-anthraquinone structure.

The 1976 article describes purification of Factors II, VII, IX and X from human plasma by the use of the same anthraguinone blue dye coupled to a polymer of polysaccharide. Elution with acetate buffers separated Factor X from Factors II, VII and IX. The authors indicate that one fraction of the column-bound material showed Factor IIa (thrombin) activity, indicating possible activation of Factor II to thrombin.

Both the 1970 and 1976 article describe the purification of Factor X to remove other clotting factors, e.g., II, VII and IX, as impurities. Neither article discloses or suggests the removal of pyrogens from thrombin.

There is a need for a simple and efficient method of removing pyrogens from blood protein products which can be easily adapted to a multi-liter process.

SUMMARY OF THE INVENTION

The present invention is directed to a method of removing pyrogens from bovine thrombin. The method involves the steps of forming a complex of an anthraquinone blue dye having the structure:

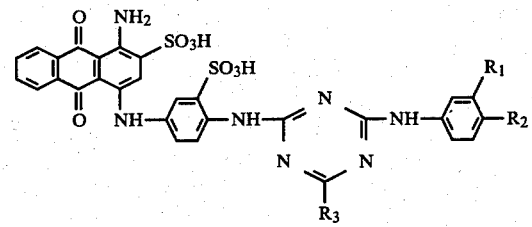

where $R_1$ and $R_2$ are hydrogen or $SO_3H$ and $R_3$ is Cl or O, and a dextran which has been cross-linked with epichlorohydrin to produce a polysaccharide, and equilibrating the complex with a low ionic strength salt solution. Pyrogen-containing bovine thrombin is placed in contact with the complex and the thrombin is washed with a low ionic strength salt solution to remove the pyrogens. Pyrogen-free bovine thrombin is recovered for example, by desorption with a high ionic strength salt solution.

DETAILED DESCRIPTION OF THE INVENTION

The impure pyrogen-containing thrombin material used in the present invention can be produced from bovine plasma containing Factor II (prothrombin) by conversion of Factor II to thrombin. Various methods have been described in the literature for obtaining thrombin. For example, prothrombin can be prepared from Factor IX concentrates. [See *J. Biol. Chem.,* 248: 7729–7741 (1973)]. The prothombin can be adsorbed onto barium citrate, eluted with ethylenediaminetetraacetic acid, fractionated with ammonium sulfate, and further purified by DEAE-cellulose chromatography. The prothombin can then be activated with bovine Factor Xa as described in *J. Biological Chemistry*, 250: 8897–8906 (1975).

The method used to prepare the thrombin-containing starting material is described below.

A non-sterile prothombin complex was fractionated from bovine plasma by ion-exchange procedures. Fibrinogen and other contaminants were removed by precipitation and the prothombin was activated with beef thromboplastin and Ca++ ions.

*Arch. Biochem.*, 5: 265 (1944) describes the use of thromboplastin and calcium, strontium, magnesium or barium salts. *J. Biol. Chem.*, 246: 6106–6114 (1971) describes activation of prothrombin with sodium citrate, followed by dialysis.

The thrombin material was then subjected to high speed centrifugation to clarify the complex and subsequently subjected to macroporous and microporous membrane filtration. As indicated earlier, various methods for producing thrombin have been taught in the art. These methods can be used to obtain the starting material used in the present invention. It is this pyrogen-containing thrombin that is used in the method of the present invention.

An anthraquinone blue dye, having the structure:

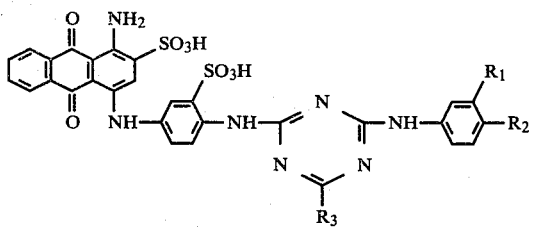

where $R_1$ and $R_2$ are hydrogen or $SO_3H$ and $R_3$ is Cl or O, was bound to a dextran which has been cross-linked with epichlorohydrin to produce a three dimensional network of polysaccharides. A suitable blue dye-polysaccharide matrix where $R_3$ is Cl, is commercially available from Pharmacia, Uppsala, Sweden under the trade designation Blue Sepharose CL6B. A suitable blue dye where $R_3$ is O, is commercially available from Ciba AG, Basel, Switzerland, under the trade designation Cibracon Blue F3G-A. Suitable polysaccharides are commercially available from Pharmacia under the trade designations Sephadex type G.

The dye was bound to the polysaccharide by methods well-known in the art [See *J. Chromatography*, 69: 209–214 (1972)]. The dye and the polysaccharide can be mixed together in aqueous solution, and a sodium salt added. The low purity bovine thrombin obtained as described previously was then applied to a column composed of the blue dye-polysaccharide complex equilibrated with a low ionic strength salt solution, e.g., 0.10 to 0.20 M NaCl. The thrombin is placed in contact with the complex for a time sufficient to allow binding of the thrombin to the complex. The binding takes place upon contact, and washing with the equilibrating solution is carried out immediately after contact. The thrombin was then washed with the equilibrating solution and the pyrogens were removed in the wash solution. The purified thrombin was then removed from the column by desorbing the column with a high ionic strength salt solution, e.g., 0.4 to 2.0 M NaCl.

EXAMPLE 1

A solution of 2 gm of an anthraquinone blue dye having the structure shown previously, where $R_3$ is O in 60 ml of water was added dropwise with vigorous stirring into a suspension of 10 gm of Sephadex G-75 in 350 ml of water at a temperature of 60° C., and stirred for 30 minutes. A 45 gm portion of NaCl was added and the stirring continued for one hour. The mixture was then heated to 80° C., treated with 4 gm of $Na_2CO_3$ and stirred for an additional hour at this temperature. After cooling to room temperature, the gel was filtered by suction in a Büchner funnel and washed with water.

The gel was packed into a column (10 cm) equilibrated with a 0.2 M NaCl solution at a pH in the range of about 6 to 8.

A thrombin preparation prepared as described earlier, containing pyrogenic material, having an initial purity of about 3 percent thrombin, was applied to the gel column. The thrombin was then washed with the low ionic strength salt equilibrating solution to remove the pyrogens. The presence of pyrogenic material in the wash solution passing through the column was tested by a procedure designated as "Limulus Amebocyte Lysate," based on a test described in *Biochemica. et Biophysica. Acta.*, 261: 284–289 (1972).

After the solution tested negative for the presence of pyrogenic material, the thrombin was desorbed from the gel column by contacting the gel column with a high ionic strength salt solution, i.e., a 2 M NaCl solution. The thrombin had a purity of about 70 percent. The thrombin desorbed from the gel column was then dialyzed against 0.15 M NaCl, sterile-filtered and freeze-dried.

The thrombin obtained was tested by the pyrogen-rabbit test referred to earlier and determined to be pyrogen-free, and suitable for use as a topically-administered blood clotting agent.

Thrombin may also have associated therewith enzymes and pro-enzymes, e.g., plasmin and plasminogen. The substances are involved in the clotting process, specifically in the lysis of thrombi. Preliminary tests of the thrombin prepared as described above indicate that the above procedure removes plasmin and plasminogen from the bovine thrombin.

What is claimed is:

1. A method for removing pyrogenic material from pyrogen-containing bovine thrombin which comprises the steps of forming a complex of a dye having the structure:

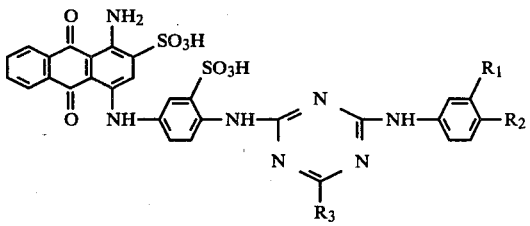

where $R_1$ and $R_2$ are hydrogen or $SO_3H$, and $R_3$ is Cl or O; and a dextran which has been cross-linked with epichlorohydrin to produce a three-dimensional network of polysaccharides, equilibrating the complex with a low ionic strength salt solution, contacting said complex with said pyrogen-containing bovine thrombin, washing said thrombin with a low ionic strength salt solution to remove said pyrogens, and recovering pyrogen-free bovine thrombin.

2. The method of claim 1 wherein the low ionic strength salt solution used to equilibrate the complex has an ionic strength not greater than 0.20.

3. The method of claim 2 wherein the low ionic strength salt solution used to wash the thrombin is the same as that used to equilibrate the dyepolysaccharide complex.

4. The method of claim 1 wherein recovering pyrogen-free bovine thrombin comprises treating the thrombin with a salt solution of ionic strength sufficient to remove the thrombin from the complex, and collecting the pyrogen-free bovine thrombin.

5. The method of claim 4 wherein the salt solution used to remove the thrombin from the complex has an ionic strength not less than 0.4.

6. The method of claim 5 wherein the low ionic strength salt solution and the salt solution used to remove the thrombin both contain NaCl.

* * * * *